(12) United States Patent
Becker et al.

(10) Patent No.: US 7,740,829 B2
(45) Date of Patent: Jun. 22, 2010

(54) SYNTHESIS GAS PRODUCTION AND USE

(75) Inventors: Christopher L. Becker, Russell, KS (US); Frank Hershkowitz, Liberty Corner, NJ (US); James Richardson Lattner, LaPorte, TX (US)

(73) Assignee: ExxonMobil Research & Engineering Company, Annandale, NJ (US)

( * ) Notice: Subject to any disclaimer, the term of this patent is extended or adjusted under 35 U.S.C. 154(b) by 1028 days.

(21) Appl. No.: 11/477,504

(22) Filed: Jun. 29, 2006

(65) Prior Publication Data

US 2007/0003478 A1 Jan. 4, 2007

Related U.S. Application Data

(60) Provisional application No. 60/695,733, filed on Jun. 29, 2005.

(51) Int. Cl.
*C01B 3/24* (2006.01)
*C01B 3/26* (2006.01)

(52) U.S. Cl. .................................. 423/650; 423/652

(58) Field of Classification Search .................. 423/650
See application file for complete search history.

(56) References Cited

U.S. PATENT DOCUMENTS

| | | | |
|---|---|---|---|
| 4,240,805 A | 12/1980 | Sederquist | |
| 5,653,774 A * | 8/1997 | Bhattacharyya et al. | .... 48/198.7 |
| 6,767,530 B2 * | 7/2004 | Kobayashi et al. | .......... 423/650 |

2002/0062943 A1 5/2002 Kondo et al.

FOREIGN PATENT DOCUMENTS

| EP | 0 953 543 A2 | 4/1999 |
|---|---|---|
| EP | 0953543 A2 | 11/1999 |
| GB | 2 187 751 A | 3/1986 |
| GB | 2187751 A | 9/1987 |
| WO | WO 03/051771 A1 | 6/2003 |
| WO | WO 03051771 A1 | 6/2003 |

OTHER PUBLICATIONS

Y. Matros, et al. "Reverse-Flow Operation in Fixed Bed Catalytic Reactors", *Catal. Rev.—Sci. Eng.*, 38(1), 1996, pp. 1-68.
B. Glockler, et al., "Analysis of a Novel Reverse-Flow Reactor Concept for Autothermal Methane Steam Reforming", *Chemical Engineering Science*, 58, 2003, pp. 593-601.
G. Kolios, et al., "Autothermal Fixed-Bed Reactor Concepts", *Chemical Engineering Science*, 55, 2000, pp. 5945-5967.
T. Kikas, et al., "Hydrogen Production in a Reverse-Flow Autothermal Catalytic Microreactor: From Evidence of Performance Enhancement to Innovative Reactor Design", *Ind. Eng. Chem. Res.*, 42, 2003, pp. 6273-6279.

(Continued)

*Primary Examiner*—Melvin C Mayes
*Assistant Examiner*—Kenneth Vaden (57) ABSTRACT

Synthesis gas is produced according to this invention using a combination of steam reforming and oxidation chemistry. The process incorporates the use of solids to heat the hydrocarbon feed, and to cool the gas product. According to the invention, heat can be conserved by directionally reversing the flow of feed and product gases at intermittent intervals.

19 Claims, 5 Drawing Sheets

OTHER PUBLICATIONS

D. Neumann, et al., "Catalytic Partial Oxidation of Methane in a High-Temperature Reverse-Flow Reactor", *AIChE Journal*, 51, No. 1, 2005, pp. 210-223.

Dirk Neumann and Gotz Veser, Catalytic Partial Oxidation of Methane in a High-Temperature Reverse-Flow Reactor, AIChE Journal, Jan. 2005, pp. 210-223, vol. 51, No. 1, American Institute of Chemical Engineers.

Timo Kikas et al, Hydrogen Production in a Reverse-Flow Autothermal Catalytic Microreactor: From Evidence of Performance Enhancement to Innovative Reactor Design, Ind. Eng. Chem. Res., 2003, pp. 6273-6279, 42, American Chemical Society.

Yurii SH. Matros and Grigori A. Bunimovich, Reverse-Flow Operation in Fixed Bed Catalytic Reactors, Catal. Rev.-Sci. Eng., 1996, pp. 1-68, 38 (1), Marcel Dekker, Inc.

Bernd Glockler, Grigorios Kolios, Gerhart Eigenberger, Analysis of a novel reverse-flow reactor concept for autothermal methane steam reforming, Chemical Engineering Science, 2003, pp. 593-601, 58, Elsevier Science Ltd.

G. Kolios, J. Frauhammer, G. Eigenberger, Review Autothermal fixed-bed reactor concepts, Chemical Engineering Science, 2000, pp. 5945-5967, 55, Elsevier Science Ltd.

A.M. De Groote and G. F. Froment and TH. Kobylinski, Synthesis Gas Production from Natural Gas in a Fixed Bed Reactor with Reversed Flow, The Canadian Journal of Chemical Engineering, Oct. 1996, pp. 735-742, vol. 74.

* cited by examiner

SYNTHESIS GAS PRODUCTION AND USE

This application claims the benefit of U.S. Provisional 60/695,733 filed Jun. 29, 2005.

FIELD OF THE INVENTION

This invention relates to the production and use of synthesis gas (syngas). In particular, this invention relates to the production of syngas using solids to heat and cool process gases.

BACKGROUND OF THE INVENTION

The reforming of hydrocarbons, such as methane or natural gas, to synthesis gas is an endothermic reaction, meaning that the reaction absorbs heat as it proceeds. In some reaction systems a combination of reforming and oxidation is carried out. In general, this combination reaction process is referred to as autothermal reforming. The advantage of including an oxidation step with a reforming step is that heat that is produced during this step can be used to drive the reforming step.

A. M. De Groote et al., in "Synthesis Gas Production from Natural Gas in a Fixed Bed Reactor with Reversed Flow," *The Canadian Journal of Chemical Engineering*, Vol. 74, October, 1996, pp. 735-742, discuss the production of synthesis by partial oxidation of natural gas on a Ni-catalyst in a fixed bed reactor with reversed flow. A one dimensional, non-steady state reactor model was used to simulate the process. The simulation projected the production of synthesis gas having a $H_2/CO$ ratio of 2.1, with a conversion of methane between 74% and 80%.

UK Patent Application, GB 2 187 751, discloses a process for producing synthesis gas by catalytic endothermic reaction of organic compounds with steam and/or carbon dioxide. The process uses thermal energy recovered from the partial oxidation of hydrocarbon fuels to carbon monoxide and hydrogen.

G. Kolios et al., in "Autothermal Fixed-Bed Reactor Concepts," *Chemical Engineering Science*, 55 (2000), 5945-5967, disclose a variety of autothermal fixed-bed reaction systems. Different reactor types are discussed, as well as basic reaction behavior, stability and nonlinear dynamic features.

Timo Kikas et al., in "Hydrogen Production in a Reverse-Flow Autothermal Catalytic Microreactor: From Evidence of Performance Enhancement to Innovative Reactor Design," *Industrial & Engineering Chemistry Research*, 42 (25): 6273-6279 Dec. 10, 2003, describe autothermal reverse-flow operation of a microreactor. The microreactor is a planar reverse-flow microreactor that integrates a mixing chamber, a zero-dead-volume rotating valve and a reaction chamber. Heat from the partial oxidation step of the reaction is used to preheat feed gasses by placing the reaction chamber inside the mixing chamber to capture the heat escaping the reaction chamber in a radial outward direction.

B. Glöcker et al., in "Analysis of a Novel Reverse-Flow Reactor Concept for Autothermal Methane Steam Reforming," *Chemical Engineering Science*, 58 (2003), 593-601, discuss asymmetric operation of a reverse-flow steam reforming reactor. Heat consumption during the endothermic step of the operation forms a temperature wave with an expansive low-temperature and a compressive high-temperature part. During the exothermic step of the operation an axial distribution of the heat supply is used in order to maintain a favorable temperature profile in the cyclic operation mode.

Yurii Matros and G. Bunimovich, in "Reverse Flow Operation in Fixed Bed Catalytic Reactors," *Catal. Rev.-Sci. Eng.*, 38(1), 1-68 (1996), discuss various arrangements of reverse flow reactors. In one arrangement, a reactant is added at an intermediate point or points in the system, and the system is particularly suited to selective catalytic reduction of $NO_x$ by ammonia.

Although a variety of autothermal reforming operation systems have been proposed in an effort to efficiently capture and reuse heat, additional and further efficient systems are sought. Systems are also sought in which more a desirable CO and $CO_2$ content of the synthesis gas products can be manufactured.

SUMMARY OF THE INVENTION

This invention provides processes for producing synthesis gases in an manner that allows for efficient recovery and reuse of heat within the system. The processes also enable the production of synthesis gases at $CO:CO_2$ ratios that are highly beneficial for producing oxygenated compounds, particularly alcohol products such as methanol.

According to one aspect of the invention, there is provided a process for producing synthesis gas. In one embodiment, the process comprises flowing a hydrocarbon and water-containing gas across a first bed of solids to heat the gas. The heated gas is then flowed across at least one reforming zone or oxidation zone to form a synthesis gas. Preferably, the gas is flowed across at least one reforming zone and at least one oxidation zone. The reforming zone and the oxidation zone can be in any order, and there may be more than one reforming zone and/or oxidation zone if desired. In one embodiment, at least one reforming zone is upstream of at least one oxidation zone. In another, at least one reforming zone is downstream of at least one oxidation zone.

In another embodiment, the hydrocarbon and water-containing gas is flowed across the first bed of solids and is contacted with an oxygen-containing gas to oxidize at least a portion of the hydrocarbon to form an oxidized gas. Optionally, prior to contacting the heated gas with the oxygen-containing gas, the heated gas is passed across a bed of reforming catalyst to form a reformed gas. Preferably, the oxidized gas is flowed across a bed of reforming catalyst to form a synthesis gas containing hydrocarbon, CO and $CO_2$. More preferably, the synthesis gas is flowed across a second bed of solids to heat the second bed of solids.

In another embodiment of the invention, a hydrocarbon and water-containing gas is flowed across a first bed of solids to heat the gas, and the heated gas is flowed across a bed of reforming catalyst to form a reformed gas containing hydrocarbon, CO and $CO_2$. Preferably, the reformed gas is contacted with an oxygen-containing gas to oxidize at least a portion of the hydrocarbon in the reformed gas and form a synthesis gas. Still more preferably, the synthesis gas is flowed across a second bed of reforming catalyst to convert at least a portion of unconverted hydrocarbon in the synthesis gas to form additional CO and $CO_2$. Ultimately, the synthesis gas from the second bed of reforming catalyst is flowed across a second bed of solids to heat the second bed of solids.

In yet another embodiment of the invention, synthesis gas that leaves the bed of reforming catalyst is maintained at a temperature of at least 900° C. In order to preserve heat, the gases being flowed across the beds of solids and reforming catalyst are directionally reversed at intermittent intervals.

In one embodiment, the gas flowed across the first bed of solids is heated to a temperature of at least 900° C. Preferably, the reforming gas that leaves the bed of reforming catalyst is maintained at a temperature of at least 750° C.

In another embodiment, the synthesis gas that leaves the second bed of solids is maintained at a temperature of not greater than about 650° C. Preferably, the reforming catalyst comprises at least one active metal or metal oxide of Group 6 or Group 8 to 10 of the Periodic Table of the Elements.

In one embodiment, the solids are refractory inorganic oxide solids. The first and/or second beds of solids can be in the same vessel as the reforming catalyst or one or more of the beds can be in separate vessels. Preferably, the hydrocarbon being processed comprises methane.

BRIEF DESCRIPTION OF THE DRAWING

Examples of various embodiments of this invention are shown in the attached Figures, wherein.

DETAILED DESCRIPTION OF THE INVENTION

I. Manufacturing Synthesis Gas

This invention is directed to a process for producing synthesis gas (or syngas) and to uses of the synthesis gas. Synthesis gas comprises carbon monoxide and hydrogen. Optionally, any one or more of carbon dioxide, water, methane and nitrogen are included. In one embodiment of the invention, the synthesis gas made according to this invention is used in the manufacture of alcohol, particularly methanol.

The synthesis gas is produced according to this invention using a combination of steam reforming and oxidation chemistry. Such a combination process is sometimes referred to as autothermal reforming. The process incorporates the use of solids to heat hydrocarbon feed. The advantage of using the solids is that there will be less heat stress imposed on metal surfaces used in the reaction system and that the solids can be used to conserve heat produced during the process. Additional solids can also be used to cool the synthesis gas product. In particular, the conservation of heat can be realized by directionally reversing the flow of feed and product gases at intermittent intervals.

According to one embodiment of the invention, hydrocarbon and water (i.e., steam) are first heated by passing or flowing the components in their gaseous state over a bed of solids. The solids contain sufficient heat that allow the hydrocarbon and water to be reformed as that mixture passes or flows across a reforming catalyst. Preferably, the hydrocarbon and water are heated to a temperature of at least about 900° C. More preferably, the hydrocarbon and water are heated to a temperature of at least about 950° C., still more preferably at least about 1000° C., and most preferably at least about 1050° C.

The heated hydrocarbon and water are then optionally passed or flowed over a bed of reforming catalyst. The hydrocarbon and water are then "reformed" or converted to a mixture of compounds that includes $H_2$, CO and $CO_2$, as well as unconverted hydrocarbon. For purposes of this invention this product is referred to as a reformed gas.

The reformed gas is cooler or lower in temperature than the heated hydrocarbon and water fed to the reforming catalyst. This is because the reforming that takes place is an endothermic reaction that consumes heat. In one embodiment, only one reforming zone is used. In another embodiment, more than one zone can be used. In one embodiment, one reforming zone is used and the reforming gas that exits or leaves that zone is maintained at a temperature of at least about 750° C., preferably at least about 800° C., and more preferably at least about 850° C.

Oxidation is an exothermic reaction process. An exothermic reaction process is one in which heat is released. Oxidized gas that emerges from an oxidation step is, therefore, relatively hot. Since the oxidized gas that emerges from an oxidation reaction is hot, it can be sent to an optional and additional reforming step if desired, with little if any additional heat need for reforming. The optional reforming step will further convert some or all of any unreacted hydrocarbon in the oxidized gas. The result will be the formation of a synthesis gas having slightly modified $CO:CO_2$ ratio from that emerging from the oxidation step. One or more reforming steps can be performed either before or after the oxidation step.

If a reforming step is used following the oxidation step, the gas sent through the subsequent reforming step should be maintained at a temperature to maximize the desired $CO:CO_2$ ratio. For example, if the temperature of the gas passing through the subsequent reforming zone drops too low, there will be a tendency for the reforming reaction to reverse causing some amount of the CO and $H_2$ present to convert back to hydrocarbon (i.e., methane). In one embodiment, the synthesis gas that leaves the subsequent reforming zone is generally maintained at a temperature of at least about 900° C. More preferably, the synthesis gas that leaves the subsequent reforming zone is generally maintained at a temperature of at least about 950° C., still more preferably at least about 1000° C., and most preferably at least about 1050° C.

In one embodiment of the invention, the synthesis gas is cooled by passing the synthesis gas across another bed of solids to absorb heat from the synthesis gas. This bed of solids is a second or different bed of solids that is used to heat the hydrocarbon and water feed. The solids used to cool the synthesis gas can be held in the same vessel as the first bed that is used to heat the hydrocarbon and water feed, or it can be held in a separate vessel. Preferably, the synthesis gas that leaves the second or final bed of solids is maintained at a temperature of not greater than about 650° C., preferably not greater than about 600° C., and most preferably not greater than about 550° C.

As the hydrocarbon and water pass across the first bed of solids, the solids will gradually cool over time. Consequently, as the hot synthesis gas is passed across the second or subsequent bed of solids, that bed will gradually heat over time. To efficiently capture the heat being removed or added, the gas being passed across the beds of solids, and any reforming catalyst that may be present, can be directionally reversed at intermittent intervals. For example, gas flow can be reversed at an interval of from about 5 seconds to 3 hours. In a preferred embodiment, the gas flow is reversed at an interval of from about 10 seconds to 1 hour, more preferably from about 20 seconds to 10 minutes.

In one embodiment, oxidation gas (i.e., gas containing oxygen) is injected into an oxidation zone for a predetermined period of time. The oxidation gas can be injected by way of any type of distribution or burner arrangement. After the predetermined period of time, the flow of oxidation gas is re-routed to another oxidation zone in response to directionally reversing the flow of gases. Preferably, the oxidation gas is injected by way of a burner into a first oxidation zone and the oxidation gas is injected by way of a second burner into a second oxidation zone corresponding to the directional reversal of gas flow through the reaction system.

II. Hydrocarbon Feed

The hydrocarbon feed stream from which the synthesis gas stream is produced according to this invention can be provided from any conventional source. For example, the hydrocarbon feed stream may include a natural or synthetic gas stream. Examples of sources of the hydrocarbon feed include biomass, natural gas, $C_1$-$C_5$ hydrocarbons, naphtha, or heavy petroleum oils. Preferably, the hydrocarbon feed is a gas stream comprising methane in an amount of at least about 50% by volume, more preferably at least about 70% by volume, most preferably at least about 80% by volume, based on total volume of the hydrocarbon stream. In one embodiment of this invention, the hydrocarbon feed is a natural gas comprising at least 50% methane by volume.

III. Heat Transfer Solids

Heat transfer solids that can be used in this invention include, for example, refractory inorganic oxide solids. Examples of suitable refractory inorganic oxide solids include alkaline-earth metal oxides, aluminates, and spinels. Particularly preferred compounds include magnesia, magnesium aluminate, strontium aluminate, barium aluminate, zirconia, and alumina, especially alpha alumina.

In one embodiment, the heat transfer solids contain not greater than about 2 percent, preferably not greater than about 1 percent, and more preferably not greater than about 0.5 percent silicon, based on the total weight of the solids. In another embodiment, the heat transfer solids contain not greater than about 1,500 parts per million parts by weight boron, preferably not greater than about 1,000 parts per million parts by weight boron, and more preferably not greater than about 500 parts per million parts by weight boron, based on total weight of the solids.

The heat transfer solids preferably have little to no catalytic activity. That is, the heat transfer solids are essentially ineffective in the catalytic hydrogenation of CO or $CO_2$ to methane. The heat transfer solids preferably have a surface area, as measured by nitrogen BET, of not greater than 10 m$^2$/g, more preferably not greater than 5 m$^2$/g, and most preferably not greater than 2 m$^2$/g. In one embodiment, the heat transfer solids have a Group 6-8 metals content of not greater than 0.5%, preferably not greater than 0.2%, and most preferably not greater than 0.1% by weight. The heat transfer solids may be in the form of spheres, extrudates, tablets, granules, monoliths, or otherwise structured to allow gas flow through the bed.

IV. Steam Reforming Step

The steam reforming step is preferably carried out using a reforming catalyst. In this step, the hydrocarbon feed is converted to a mixture of $H_2$, CO and $CO_2$ by reacting hydrocarbons with steam over a catalyst. This process involves the following reactions:

$$CH_4 + H_2O \leftrightharpoons CO + 3H_2 \qquad (1)$$

or $$C_nH_m + nH_2O \leftrightharpoons nCO + [n+(m/2)]H_2 \qquad (2)$$

and $$CO + H_2O \leftrightharpoons CO_2 + H_2 \qquad (3) \text{ (shift reaction)}$$

The catalyst used in the step of catalytic steam reforming generally comprises at least one active metal or metal oxide of Group 6 or Group 8 to 10 of the Periodic Table of the Elements. The Periodic Table of the Elements referred to herein is that from *CRC Handbook of Chemistry and Physics*, 82$^{nd}$ Edition, 2001-2002, CRC Press LLC, which is incorporated herein by reference.

In one embodiment, the catalyst contains at least one Group 6 or Group 8-10 metal, or oxide thereof, having an atomic number of 28 or greater. Specific examples of reforming catalysts that can be used are nickel, nickel oxide, cobalt oxide, chromia and molybdenum oxide. Optionally, the catalyst is employed with least one promoter. Examples of promoters include alkali and rare earth promoters. Generally, promoted nickel oxide catalysts are preferred.

The amount of Group 6 or Group 8 to 10 metals in the catalyst can vary. Preferably, the catalyst includes from about 3 wt % to about 40 wt % of at least one Group 6 or Group 8 to 10 metal, based on total weight of the catalyst. Preferably, the catalyst includes from about 5 wt % to about 25 wt % of at least one Group 6 or Group 8 to 10 metal, based on total weight of the catalyst.

The reforming catalyst optionally contains one or more metals to suppress carbon deposition during steam reforming. Such metals are selected from the metals of Group 14 and Group 15 of the Periodic Table of the Elements. Preferred Group 14 and Group 15 metals include germanium, tin, lead, arsenic, antimony, and bismuth. Such metals are preferably included in the catalyst in an amount of from about 0.1 wt % to about 30 wt %, based on total weight of nickel in the catalyst.

In a catalyst comprising nickel and/or cobalt there may also be present one or more platinum group metals, which are capable of increasing the activity of the nickel and/or cobalt and of decreasing the tendency to carbon lay-down when reacting steam with hydrocarbons greater than methane. The concentration of such platinum group metal is typically in the range 0.0005 to 0.1% as metal, calculated as the whole catalyst unit. Further, the catalyst, especially in preferred forms, can contain a platinum group metal but no non-noble catalytic component. Such a catalyst is more suitable for the hydrocarbon steam reforming reaction than one containing a platinum group metal on a conventional support because a greater fraction of the active metal is accessible to the reacting gas. A typical content of platinum group metal when used alone is in the range 0.0005 to 0.5% w/w as metal, calculated on the whole catalytic unit.

In one embodiment, a bed of solid catalyst granules is used. Preferably, the solid catalyst granules comprise nickel or other catalytic agents deposited on a suitable inert carrier material. More preferably, the catalyst is NiO supported on calcium aluminate, alumina, spinel type magnesium aluminum oxide or calcium aluminate titanate.

In yet another embodiment, the hydrocarbon feedstock is preheated across the solids bed up to as high a temperature as is consistent with avoiding undesired pyrolysis or other heat deterioration. Since steam reforming is endothermic in nature, and since there are practical limits to the amount of heat that can be added by indirect heating in the reforming zones, preheating of the feed is desired to facilitate the attainment and maintenance of a suitable temperature within the reformer itself. In still other embodiments, it is desirable to preheat both the hydrocarbon feed and the steam to a temperature of at least 400° C. Preferably, the reforming reaction is generally carried out at a reformer zone temperature of from about 500° C. to about 1,200° C., preferably from about 800° C. to about 1,100° C., and more preferably from about 900° C. to about 1,050° C.

Gas hourly space velocity in the reforming zone should be sufficient to allow the reaction to approach thermodynamic equilibrium with respect to methane, CO, $CO_2$, and $H_2O$. Preferably, the gas hourly space velocity (based on wet feed) is from about 3,000 per hour to about 10,000 per hour, more preferably from about 4,000 per hour to about 9,000 per hour, and most preferably from about 5,000 per hour to about 8,000 per hour.

The ratio of steam to hydrocarbon feed will vary depending on the overall conditions in the reformer. The amount of steam employed is influenced by the requirement of avoiding carbon deposition on the catalyst, and by the acceptable methane content of the effluent at the reforming conditions maintained. On this basis, the mole ratio of steam to hydrocarbon fed to at least one reforming zone, preferably a first reforming zone, more preferably a first reforming zone upstream of at least one oxidation zone, is preferably from about 0.4:1 to about 5:1, preferably from about 0.5:1 to about 4:1.

The hydrogen to carbon oxide ratio of the gas produced in at least one reforming zone, preferably a first reforming zone, more preferably a first reforming zone upstream of at least one oxidation zone, will vary depending on the overall conditions of the reformer. Preferably, the molar ratio of hydrogen to carbon oxide in the synthesis gas will range from about 1:1 to about 5:1. More preferably the molar ratio of hydrogen to carbon oxide will range from about 2:1 to about 3:1. Even more preferably the molar ratio of hydrogen to carbon oxide will range from about 2:1 to about 2.5:1. Most preferably the molar ration of hydrogen to carbon oxide will range from about 2:1 to about 2.3:1.

The steam reforming reaction is generally carried out at super-atmospheric pressure. The specific operating pressure employed is influenced by the pressure requirements of the subsequent process in which the reformed gas mixture is to be employed. Although any super-atmospheric pressure can be used in practicing the invention, pressures of from about 175 psig (1,308 kPa abs.) to about 1,100 psig (7,686 kPa abs.) are desirable. Preferably, the steam reforming step is carried out at a pressure of from about 300 psig (2,170 kPa abs.) to about 800 psig (5,687 kPa abs.), more preferably from about 350 psig (2,515 kPa abs.) to about 700 psig (4,928 kPa abs.).

In one embodiment of the invention, the hydrocarbon feed is pre-reformed prior to contacting the first bed of solids. In this embodiment, hydrocarbon feed and water are contacted with a reforming catalyst. However, the pre-reforming step is carried out at a temperature that is lower than that of a typical reforming zone. Preferably, the average reaction temperature in the pre-reforming step is at least about 50° C. lower than the average reaction temperature of the reforming zone. More preferably, the average reaction temperature in the pre-reforming step is at least about 100° C. lower, more preferably at least about 150° C. lower, than the average reaction temperature of the reforming zone. Preferably, the pre-reforming step is carried out at an average reaction temperature of from 300° C. to 500° C.

V. Oxidation Step

The invention further provides for the production of synthesis gas, or CO and $H_2$, by an oxidative conversion step. According to this step, hydrocarbon that has been reformed across a reforming catalyst is contacted with an oxygen-containing gas to form additional CO, $CO_2$ and $H_2$. The process step is exothermic, and is essentially an incomplete combustion reaction, having the following general formula:

$$C_nH_m + (n/2)O_2 \leftrightarrows nCO + (m/2)H_2 \quad (4)$$

The oxidation step is preferably carried out without the use of a catalyst, so the step is preferably considered non-catalytic oxidation. The oxidation step is carried out by injecting an oxygen-containing gas through a burner type device into a combustion chamber through which the reformed gas from the reforming step is passed. Air is suitable for use as the oxygen-containing gas. Substantially pure oxygen as the oxygen-containing gas is preferred on occasions where there is a need to avoid handling large amounts of inert gas such as nitrogen. Steam can optionally be injected.

In one embodiment of the invention, the individual components sent to the oxidation zone are introduced at a burner where they meet in a diffusion flame, producing oxidation products and heat. In the combustion chamber, oxidation of the hydrocarbons generally occurs with less than stoichiometric oxygen at very high temperatures and pressures. Preferably, the process step is carried out at a temperature and pressure that result in reduced reaction or oxidation time. The process is preferably carried out at a temperature of from about 1,350° C. to about 1,600° C., and at a pressure of from above atmospheric to about 150 atm.

In another embodiment of the invention, the reformed gas that is to be oxidized comprises methane. The reformed gas is preferably injected with oxygen into the oxidation zone at a carbon (CO, $CO_2$, or $CH_4$) to oxygen (i.e., $O_2$) ratio of from about 1.2:1 to about 10:1. Preferably the reformed gas and oxygen are injected into the reformer at a methane to oxygen ratio of from about 1.6:1 to about 8:1, more preferably from about 1.8:1 to about 4:1.

VI. Making Methanol with Synthesis Gas

The synthesis gas made according to this invention is preferably sent to an oxygenate synthesis process (i.e., a carbon oxide conversion process) and converted to an oxygenate composition. Preferably, the synthesis gas is sent to a methanol synthesis gas process for converting into a methanol composition, which optionally includes other oxygenates. The methanol synthesis gas process is accomplished in the presence of a methanol synthesis catalyst.

In one embodiment, the synthesis gas is sent "as is" to the methanol synthesis process. In another embodiment, the hydrogen, carbon monoxide, and/or carbon dioxide content of the synthesis gas is adjusted for efficiency of conversion. Desirably, the synthesis gas input to the methanol synthesis reactor has a molar ratio of hydrogen ($H_2$) to carbon oxides (CO+$CO_2$) in the range of from about 0.5:1 to about 20:1, preferably in the range of from about 2:1 to about 10:1. In another embodiment, the synthesis gas has a molar ratio of hydrogen ($H_2$) to carbon monoxide (CO) of at least 2:1. Carbon dioxide is optionally present in an amount of not greater than 50% by weight, based on total weight of the synthesis gas.

Desirably, the stoichiometric molar ratio is sufficiently high so as maintain a high yield of methanol, but not so high as to reduce the volume productivity of methanol. Preferably, the synthesis gas fed to the methanol synthesis process has a stoichiometric molar ratio (i.e., a molar ratio of ($H_2$−$CO_2$)/

(CO+CO$_2$)) of from about 1.5:1 to about 2.7:1, more preferably from about 1.8 to about 2.0, more preferably a stoichiometric molar ratio of from about 2.0:1 to about 2.2:1.

The CO$_2$ content, relative to that of CO, in the synthesis gas should be high enough so as to maintain an appropriately high reaction rate and to minimize the amount of undesirable by-products such as paraffins. At the same time, the relative CO$_2$ to CO content should not be too high so as to reduce methanol yield and generate byproduct water. Desirably, the synthesis gas contains CO$_2$ and CO at a ratio of from about 0.05 to about 1.0, preferably from about 0.1 to about 0.5.

In one embodiment, the catalyst used in the methanol synthesis process includes an oxide of at least one element selected from the group consisting of copper, silver, zinc, boron, magnesium, aluminum, vanadium, chromium, manganese, gallium, palladium, osmium and zirconium. Preferably, the catalyst is a copper based catalyst, more preferably in the form of copper oxide.

In another embodiment, the catalyst used in the methanol synthesis process is a copper based catalyst, which includes an oxide of at least one element selected from the group consisting of silver, zinc, boron, magnesium, aluminum, vanadium, chromium, manganese, gallium, palladium, osmium and zirconium. Preferably, the catalyst contains copper oxide and an oxide of at least one element selected from the group consisting of zinc, magnesium, aluminum, chromium, and zirconium. More preferably, the catalyst contains oxides of copper and zinc.

In yet another embodiment, the methanol synthesis catalyst comprises copper oxide, zinc oxide, and at least one other oxide. Preferably, the at least one other oxide is selected from the group consisting of zirconium oxide, chromium oxide, vanadium oxide, magnesium oxide, aluminum oxide, titanium oxide, hafnium oxide, molybdenum oxide, tungsten oxide, and manganese oxide.

In various embodiments, the methanol synthesis catalyst comprises from about 10 wt % to about 70 wt % copper oxide, based on total weight of the catalyst. Preferably, the methanol synthesis contains from about 15 wt % to about 68 wt % copper oxide, and more preferably from about 20 wt % to about 65 wt % copper oxide, based on total weight of the catalyst.

In one embodiment, the methanol synthesis catalyst comprises from about 3 wt % to about 30 wt % zinc oxide, based on total weight of the catalyst. Preferably, the methanol synthesis catalyst comprises from about 4 wt % to about 27 wt % zinc oxide, more preferably from about 5 wt % to about 24 wt % zinc oxide.

In embodiments in which copper oxide and zinc oxide are both present in the methanol synthesis catalyst, the ratio of copper oxide to zinc oxide can vary over a wide range. Preferably in such embodiments, the methanol synthesis catalyst comprises copper oxide and zinc oxide in a Cu:Zn atomic ratio of from about 0.5:1 to about 20:1, preferably from about 0.7:1 to about 15:1, more preferably from about 0.8:1 to about 5:1.

In one embodiment, the synthesis gas formed in the synthesis gas conversion plant is cooled prior to sending to the methanol synthesis reactor. Preferably, the synthesis gas is cooled so as to condense at least a portion of the water vapor formed during the synthesis gas process.

The methanol synthesis process used to manufacture the methanol composition of this invention can be any conventional process. Examples of such processes include batch processes and continuous processes. Continuous processes are preferred. Tubular bed processes and fluidized bed processes are particularly preferred types of continuous processes.

In general, the methanol synthesis process takes place according to the following reactions:

$$CO + 2H_2 \rightarrow CH_3OH \quad (5)$$

$$CO_2 + 3H_2 \rightarrow CH_3OH + H_2O \quad (6)$$

The methanol synthesis process is effective over a wide range of temperatures. In one embodiment, the synthesis gas is contacted with the methanol synthesis catalyst at a temperature in the range of from about 150° C. to about 450° C., preferably in a range of from about 175° C. to about 350° C., more preferably in a range of from about 200° C. to about 300° C.

The process is also operable over a wide range of pressures. In one embodiment, the synthesis gas is contacted with the methanol synthesis catalyst at a pressure in the range of from about 15 atmospheres to about 125 atmospheres, preferably in a range of from about 20 atmospheres to about 100 atmospheres, more preferably in a range of from about 25 atmospheres to about 75 atmospheres.

Gas hourly space velocities can vary as desired. Preferably, gas hourly space velocity of flow of gas through the catalyst bed is in the range of from about 50 hr$^{-1}$ to about 50,000 hr$^{-1}$. Preferably, gas hourly space velocity of flow of gas through the catalyst bed is in the range of from about 250 hr$^{-1}$ to about 25,000 hr$^{-1}$, more preferably from about 500 hr$^{-1}$ to about 10,000 hr$^{-1}$.

In one embodiment of the invention, crude methanol is produced from the methanol synthesis process. The crude methanol is then processed to form a methanol feed. Preferably, the methanol feed is of sufficiently high quality to use a feed in a catalytic methanol conversion reaction to form light olefins, particularly substantial amounts of ethylene and propylene.

Processing of the crude methanol can be accomplished using numerous means. Examples of such means include distillation, selective condensation, and selective adsorption. Process conditions, e.g., temperatures and pressures, can vary according to the particular methanol composition desired. It is particularly desirable to minimize the amount of water and light boiling point components in the methanol composition, but without substantially reducing the amount of methanol and desirable aldehydes and/or other desirable alcohols also present.

In one embodiment, the crude methanol product from the methanol synthesis reactor is further treated to reduce water content and other undesirable impurities prior to converting to olefin product. Conventional treatment processes can be used. Examples of such processes include distillation, selective condensation, and selective adsorption.

In one embodiment, a crude methanol stream comprising methanol, dimethyl ether, fusel oils (i.e., hydrocarbons and oxygenates having a boiling point greater than methanol), and water is withdrawn from a carbon oxide conversion zone. The crude methanol stream is then passed to a distillation column, conventionally referred to as a topping column. Desirably, the topping column operates at a pressure of from about 20 kPa to about 200 kPa. Preferably, the topping column operates at a pressure of from about 25 kPa to about 150 kPa, more preferably from about 30 kPa to about 125 kPa, and most preferably from about 40 kPa to about 100 kPa.

A first light ends stream is removed from an upper portion of the topping column. Preferably, the lights ends stream contains dissolved gases (e.g., hydrogen, methane, carbon oxides, and nitrogen), and light ends (e.g., ethers, ketones, and aldehydes). In one embodiment of the invention, the dissolved gases, the light ends, or both are used as fuel. In another embodiment, the dissolved gases, light ends, or both are sent to a synthesis gas production zone to produce additional synthesis gas, which can ultimately be converted to additional methanol, preferably further converted to olefin(s).

A bottoms stream is preferably removed from a lower portion of the topping column, and passed to a second distillation column, conventionally referred to as a refining column. From the refining column, a second light ends stream is withdrawn, preferably at an upper portion of the refining column. In one embodiment, the second light ends stream is combined with the first light ends stream from the topping column to form a combined purge stream. The combined purge stream is preferably used for fuel.

The refining column operates at a pressure of from about 0.5 atm to about 10 atm. Preferably, the refining column operates at a pressure of from about 0.6 to about 5 atm, more preferably from about 0.7 to about 3 atm, and most preferably from about 0.7 to about 2 atm. The refining column is used to further separate methanol from water and fusel oils, which remain in the bottoms stream of the topping column, so as to provide a high purity methanol stream, a fusel oil stream, and a water stream.

The methanol stream separated from the refining column is suitable for use in any system that uses methanol as a feedstream. Preferably, the methanol is suitable for use in an oxygenate conversion system.

In one embodiment, the methanol stream separated from the refining column comprises at least 98 wt % methanol, based on total weight of the methanol stream. Preferably, the methanol stream comprises at least 98.5 wt % methanol, more preferably at least 99.0 wt % methanol, and most preferably at least 99.5 wt % methanol, based on total weight of the methanol stream.

In another embodiment, the methanol stream separated from the refining column comprises less than 0.2 wt % water, based on total weight of the methanol stream. Preferably, the methanol stream comprises less than 0.15 wt % water, more preferably less than 0.1 wt % water, and most preferably less than 0.05 wt % water, based on total weight of the methanol stream.

In yet another embodiment, the methanol stream separated from the refining column comprises less than 40 wppm acetone, based on total weight of the methanol stream. Preferably the methanol stream separated from the refining column comprises less than 30 wppm acetone, more preferably less than 25 wt % acetone, and most preferably less than 20 wt % acetone, based on total weight of the methanol stream.

VII. Examples of Synthesis Gas Reaction Systems

Figure 1:
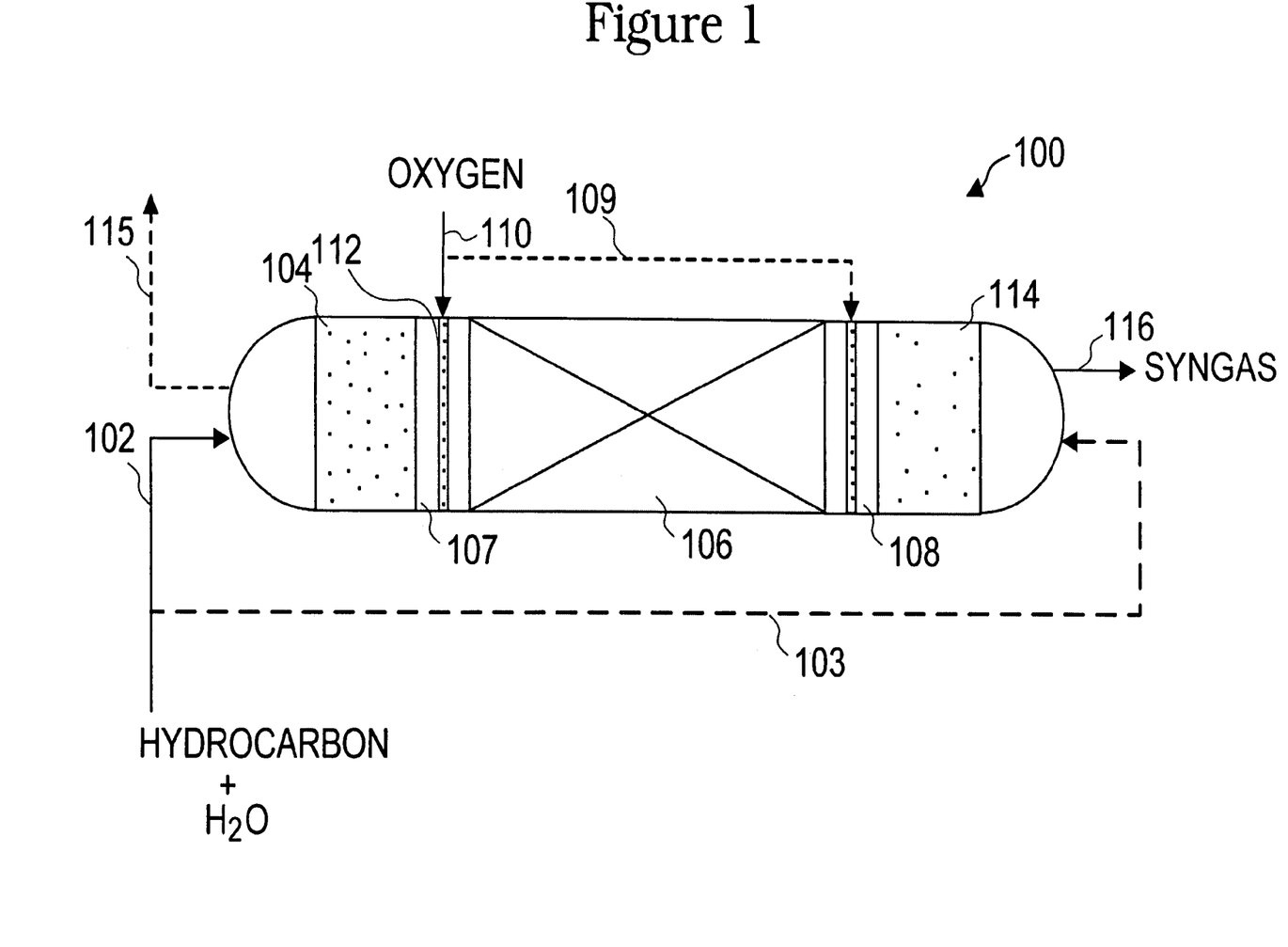
FIG. 1 shows an embodiment in which a reaction system includes two solids beds to transfer heat to and from gases flowing through the system, and includes one bed containing reforming catalyst between the solids beds.

FIG. 1 shows one embodiment of a reaction system 100 that can operate to carry out the process of the invention. According to the embodiment shown in FIG. 1, hydrocarbon and water are injected as a vapor into the reaction system 100 through a line 102. The vapor passes through a zone in the reaction system that contains a bed of solids 104, with the bed being sufficiently hot to heat the vapor to at least about 900° C. The hot vapor is then flowed to an oxidation zone 107 to contact oxygen from an oxygen-containing gas to oxidize at least a portion of the hydrocarbon in the reformed gas and form a synthesis gas. The oxygen-containing gas is sent to the oxidation zone 107 through a line 110 and distributed in the oxidation zone 107 by way of a distributor 112. Hot gas from the oxidation zone 107 is then sent to a zone 106 containing reforming catalyst. As the vapor flows through the bed of reforming catalyst, at least a portion of the hydrocarbon is converted to CO and $CO_2$. For purposes of this invention, the partially converted hydrocarbon in the vapor that exits the zone 106 is referred to as reformed gas and contains hydrocarbon CO and $CO_2$.

To cool the hot synthesis gas, it is flowed through a second bed of solids 114 that is used to absorb a substantial portion of the heat in the synthesis gas. The cooled synthesis gas then exits the system 100 through a line 116.

In order to conserve the heat transferred to and from the solids beds in the system 100, the flow of gases through the system is intermittently reversed. In the embodiment shown in FIG. 1, this is accomplished by sending the hydrocarbon and water feed to line 103 to contact the hot solids bed 114 in order to heat the hydrocarbon and water. As the gas flows through the system 100 in this direction, oxygen will then be directed through a line 109 and hot synthesis gas will be formed in oxidation zone 108 as a result. The solids in bed 104 will then be used to cool the hot synthesis gas, and the cooled synthesis gas will then exit the system 100 through a line 115.

Figure 2:
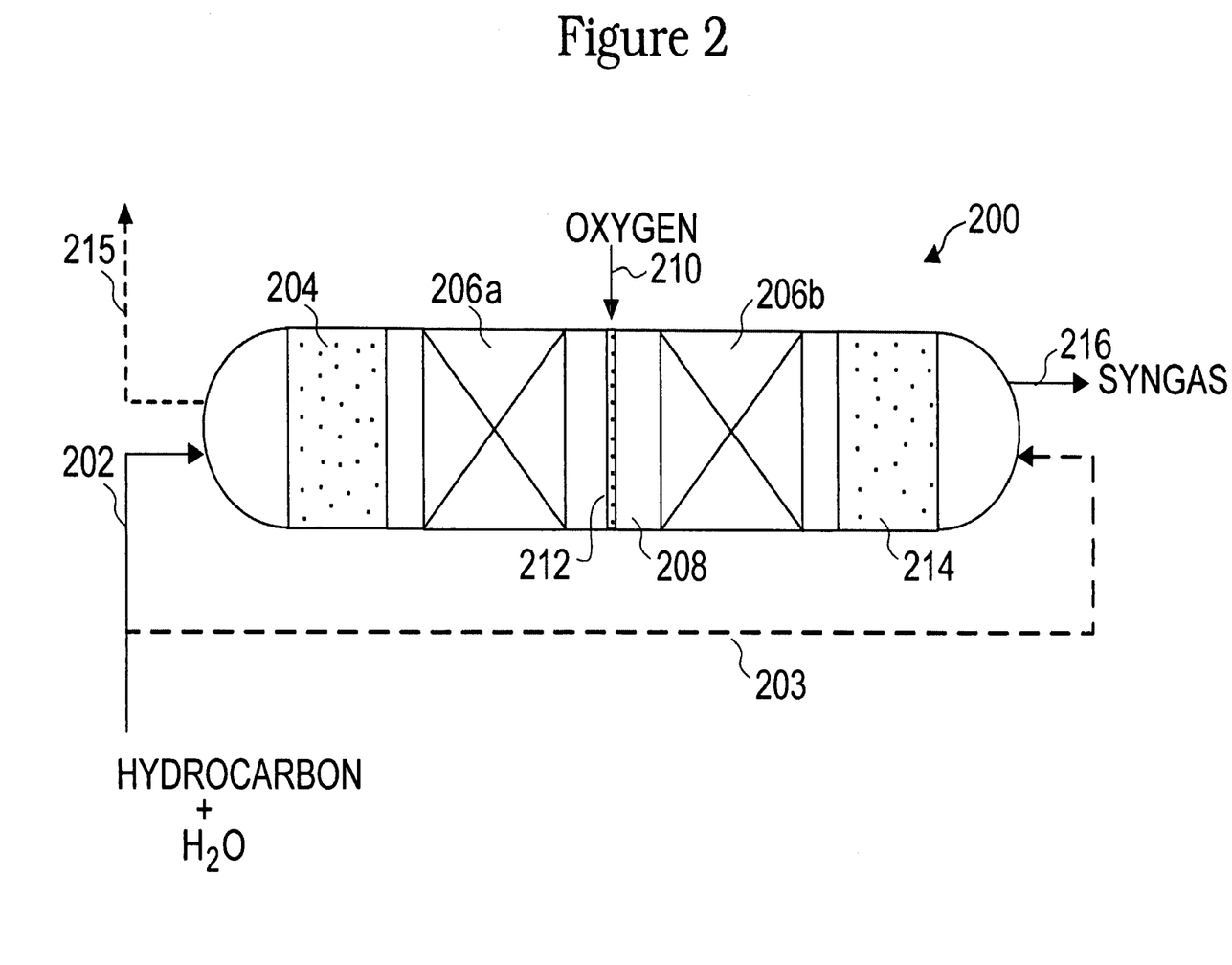
FIG. 2 shows an embodiment in which a reaction system includes two beds containing reforming catalyst that are located between two solids beds, and oxygen is added between the two reforming catalyst beds.

FIG. 2 shows an embodiment in which a reaction system 100 includes two beds, 206a and 206b, containing reforming catalyst, and oxygen is added between the two reforming catalyst beds. In this embodiment, hydrocarbon and water are injected as a vapor into the reaction system 200 through a line 202. The vapor passes through a zone in the reaction system that contains a bed of solids 204, with the bed being sufficiently hot to heat the vapor to at least about 900° C. The hot vapor is then passed to a zone 106a containing reforming catalyst. As the vapor passes through the bed of reforming catalyst, at least a portion of the hydrocarbon is converted to reformed gas as previously defined. The reformed gas is then sent to an oxidation zone 208 to contact oxygen from an oxygen-containing gas to oxidize at least a portion of the hydrocarbon in the reformed gas and form a synthesis gas. The oxygen-containing gas is sent to the oxidation zone 208 through a line 210 and distributed in the oxidation zone 208 by way of a distributor 212.

As in the embodiment of FIG. 1, the synthesis gas formed in the oxidation zone 208 is very hot as a result of the oxidation step. However, in the embodiment of FIG. 2, hydrocarbon remaining in the hot synthesis gas is further converted to $H_2$, CO and $CO_2$ by passing the hot synthesis gas through a second bed of reforming catalyst in a second reforming zone 206b. As the synthesis gas is further reformed, it is gradually cooled as a result of the reaction being endothermic. It is preferred, however, to keep the synthesis gas in the zone 206b at a temperature of at least about 900° C., in order to minimize any tendency of the CO and $H_2$ to reform hydrocarbon, i.e., $CH_4$. This synthesis gas is then passed through a second bed of solids 214 that is used to absorb a substantial portion of the heat remaining in the synthesis gas. The cooled synthesis gas then exits the system 200 through a line 216.

In order to conserve the heat transferred to and from the solids beds in the system 200, the flow of gases through the system is intermittently reversed. In the embodiment shown in FIG. 2, this is accomplished by sending the hydrocarbon and water feed to line 203 to contact the hot solids bed 214 in order to heat the hydrocarbon and water. The solids in bed 204 will ultimately be used to cool the hot synthesis gas, and the cooled synthesis gas will then exit the system 200 through a line 215.

Figure 3:
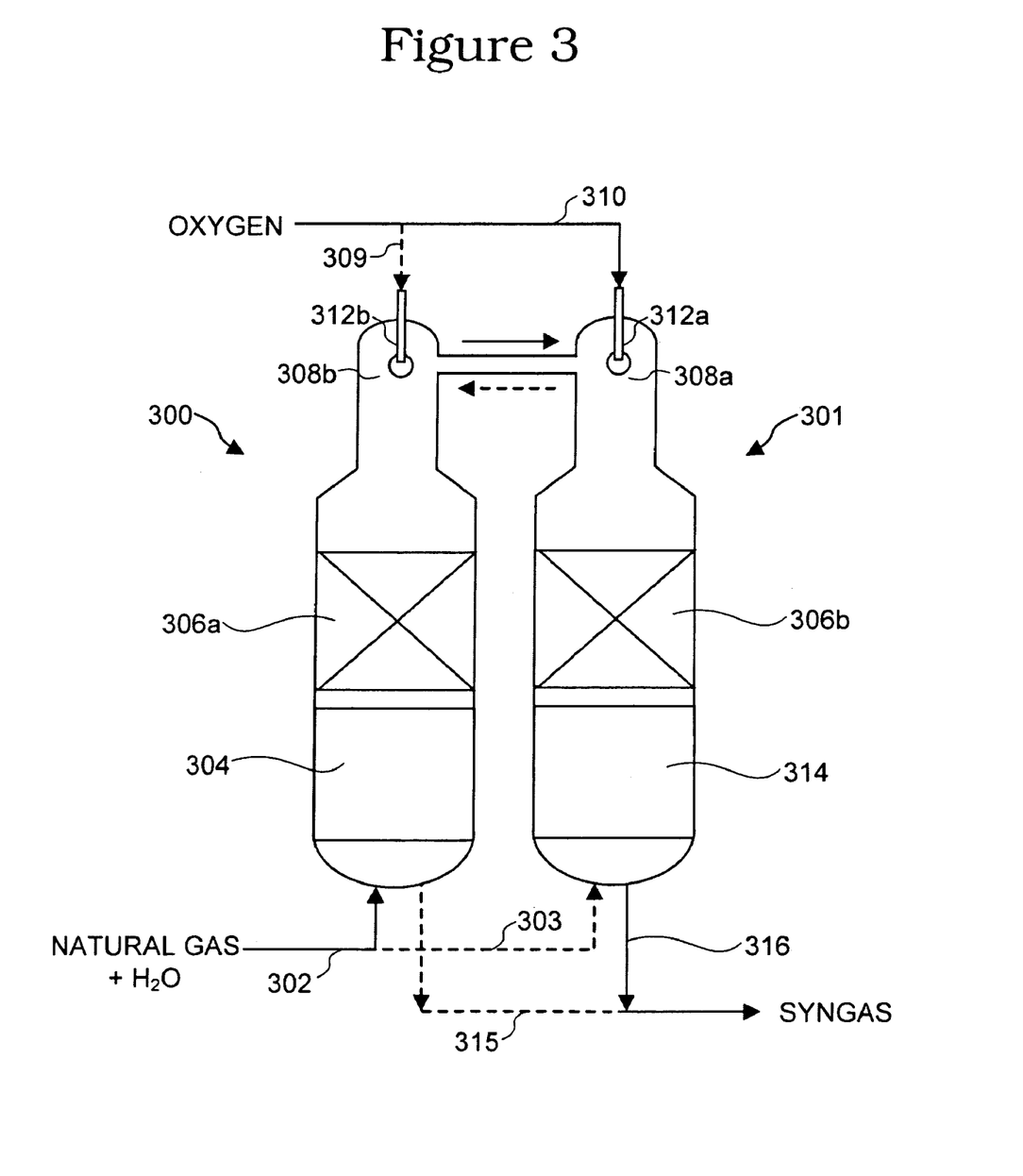
FIG. 3 shows another embodiment in which a reaction system includes two beds containing reforming catalyst that are located between two solids beds, and oxygen is added between the two reforming catalyst beds.

FIG. 3 shows a configuration that utilizes two vessels 300 and 301, and uses two beds of reforming catalyst, similar in flow scheme to that of FIG. 2. In the embodiment, in FIG. 3, hydrocarbon (e.g., natural gas) and water are injected as a vapor into the reaction vessel 300 through a line 302. The vapor passes through a zone in the reaction system that contains a bed of solids 304, with the bed being sufficiently hot to heat the vapor to at least about 900° C. The hot vapor is then passed to a zone 306a containing reforming catalyst. As the vapor passes through the bed of reforming catalyst, at least a portion of the hydrocarbon in the natural gas is converted to reformed gas as previously defined. The reformed gas is then sent to an oxidation zone 308a to contact oxygen from an oxygen-containing gas to oxidize at least a portion of the hydrocarbon in the reformed gas and form a synthesis gas. The oxygen-containing gas is sent to the oxidation zone 308a through a line 310 and distributed in the oxidation zone 308a by way of a burner assembly 312a.

At least a portion of the hydrocarbon remaining in the hot synthesis gas in oxidation zone 308a is further converted to $H_2$, CO and $CO_2$ by passing the hot synthesis gas through a second bed of reforming catalyst in a second reforming zone 306b. As the synthesis gas is further reformed, it is gradually cooled as a result of the reaction being endothermic. It is preferred, however, to keep the synthesis gas in the zone 306b at a temperature of at least about 900° C., in order to minimize any tendency of the CO and $H_2$ to reform hydrocarbon, i.e., $CH_4$. This synthesis gas is then passed through a second bed of solids 314 that is used to absorb a substantial portion of the heat remaining in the synthesis gas. The cooled synthesis gas then exits the vessel 301 through a line 316.

In order to conserve the heat transferred to and from the solids beds in the vessels 300 and 301, the flow of gases through the system is intermittently reversed. In the embodiment shown in FIG. 3, this is accomplished by sending the natural gas and water feed through a line 303 to contact the hot solids bed 314 in vessel 301 in order to heat the natural gas and water. The hot vapor is then passed through the reforming zone 306b, and gas from the reforming zone 306b is sent to the oxidation zone 308a. As the gas flows through the vessel 301 in this direction, oxygen will then be directed through a line 309 to the burner 312b, and hot synthesis gas will be formed in oxidation zone 308b as a result. The hot synthesis gas is then cooled by passing it through the bed 304. The cooled synthesis gas will then exit the vessel 300 through a line 315.

Figure 4:
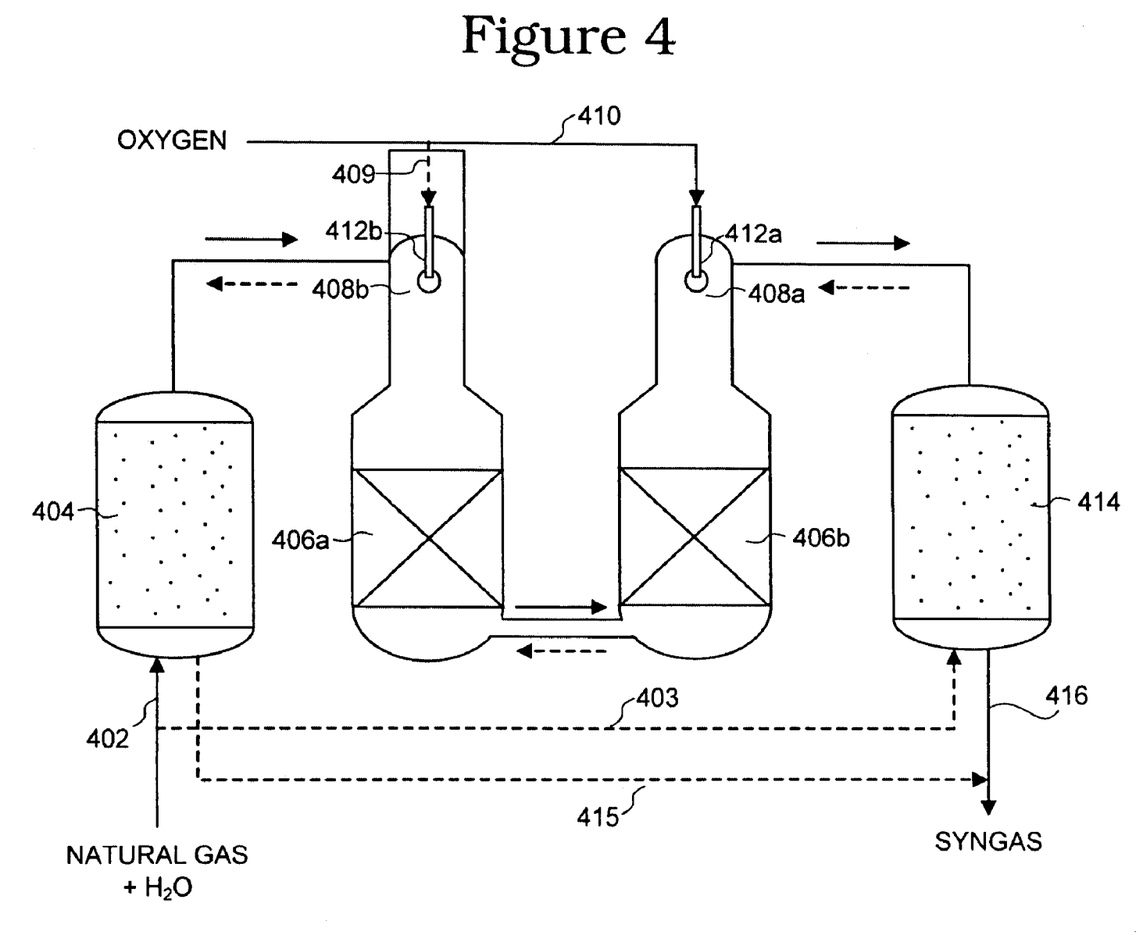
FIG. 4 shows another embodiment in which a reaction system includes two beds containing reforming catalyst that are located between two solids beds, and oxygen is added between the two reforming catalyst beds.

FIG. 4 shows a system that uses two reforming zones and two beds of solids, each in separate vessels. According to this embodiment, hydrocarbon (e.g., natural gas) and water are injected through a line 402 as a vapor, and through a zone in the vessel that contains a bed of solids 404, with the bed being sufficiently hot to heat the vapor to at least about 900° C. The hot vapor is then passed to a zone 406a containing reforming catalyst. As the vapor passes through the bed of reforming catalyst, at least a portion of the hydrocarbon in the natural gas is converted to reformed gas as previously defined. The reformed gas is then sent to a second zone 406b containing additional reforming catalyst, and the reforming reaction is continued so as to form the reformed gas as defined above. The reformed gas is then sent to an oxidation zone 408a to contact oxygen from an oxygen-containing gas to oxidize at least a portion of the hydrocarbon in the reformed gas and form a synthesis gas. The oxygen-containing gas is sent to the oxidation zone 408a through a line 410 and distributed in the oxidation zone 408a by way of a burner assembly 412a. This synthesis gas is then passed through a second bed of solids 414 that is used to absorb a substantial portion of the heat remaining in the synthesis gas. The cooled synthesis gas then exits the vessel containing the solids 414 through a line 416.

In order to conserve the heat transferred to and from the solids beds in the system shown in FIG. 4, the flow of gases through the system is intermittently reversed. This is accomplished by sending the natural gas and water feed through a line 403 to contact the hot solids bed 414 in order to heat the natural gas and water. The hot vapor is then passed through the reforming zones 406b and 406a, respectively, and gas from the reforming zone 406b is sent to the oxidation zone 408a. As the gas flows through the vessels in this direction, oxygen will then be directed through a line 409 to the burner 412b, and hot synthesis gas will be formed in oxidation zone 408b as a result. The hot synthesis gas is then cooled by passing it through the bed 404. The cooled synthesis gas will then exit the vessel containing the bed 404 through a line 415.

An advantage of the configuration shown in FIG. 3 and 4 is that 2 burners are utilized. One burner is used while the gas is flowing in one direction, and the other is used when the gas is flowing in the other direction. In other words, each burner operates with the gas flowing in just one direction, which allows the use of commercial ATR burner designs.

Figure 5:
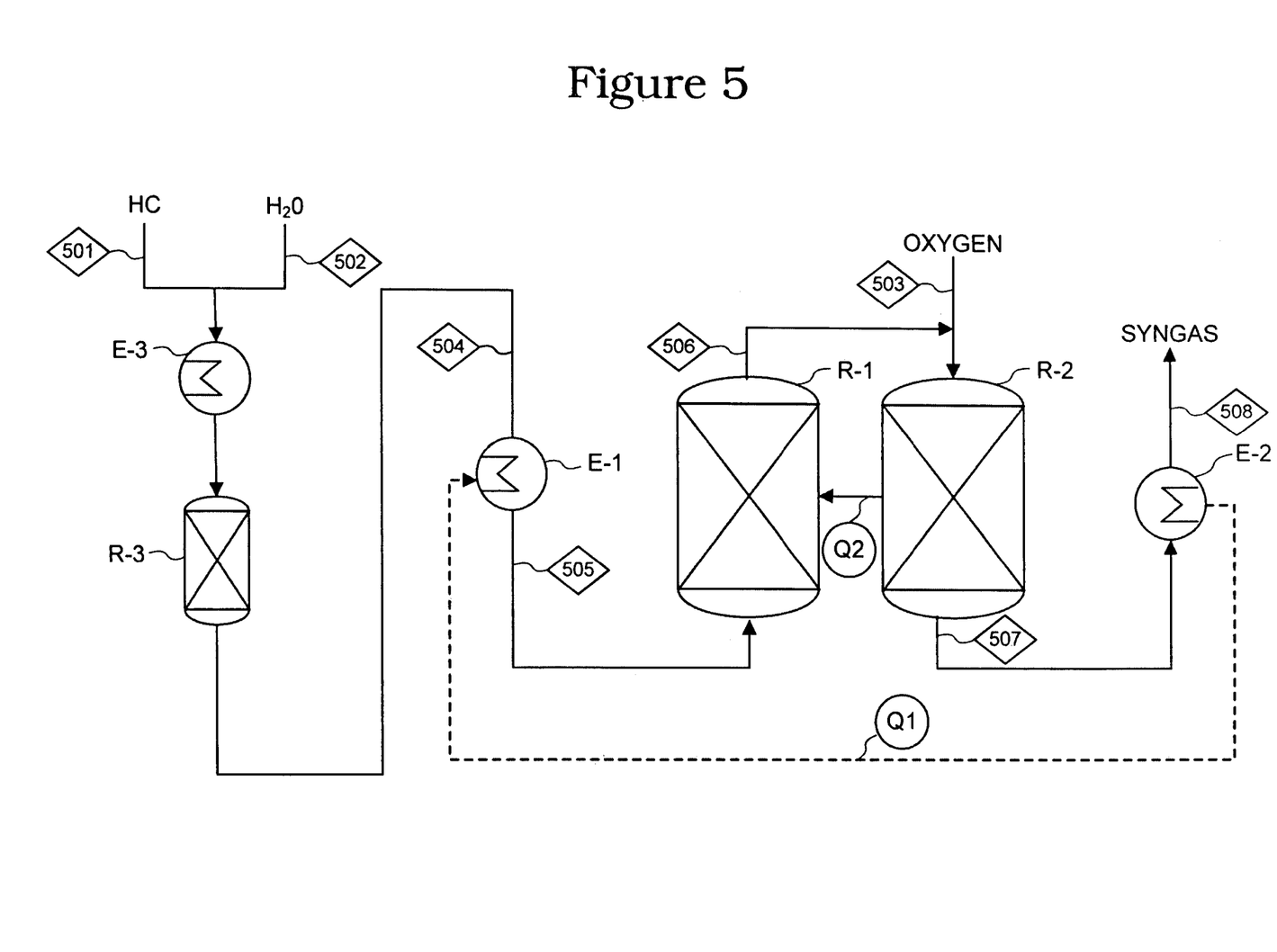
FIG. 5 shows a process scheme in which reaction and heat transfer between beds of solids and reforming catalyst were computer modeled.

A computer-based model (Pro/II® by Simulation Sciences) was used to simulate a process of the invention as shown in FIG. 5. In the figure, process streams are labeled with diamonds and energy streams are labeled with circles. According to FIG. 5, hydrocarbon (HC) feed stream 501 mixes with water (steam) stream 502. The mixture is heated to 350° C. in a heat exchanger E-3, and is then pre-reformed in reactor R-3. The pre-reforming step uses steam to convert the $C_2$+ hydrocarbons to methane. Effluent from the pre-reformer, stream 504, enters a first heat transfer bed, represented in FIG. 5 as E-1, with energy stream Q1 being used to supply heat for E-1. Stream 505 leaves E-1 and enters a first bed of reforming catalyst, R-1. The reactions in R-1 are calculated from thermodynamic equilibrium, where energy stream Q2 is added to the reactants in stream 505 to produce an equilibrated effluent stream 506. Oxygen is added via stream 503, and this composition is allowed to come to thermodynamic equilibrium with removal of heat as energy stream Q2. Equilibrated effluent stream 507 is then cooled by passing through a bed of solids, represented as E-2, with removal of heat as energy stream Q1, producing a syngas product stream 508. Various stream characteristics are shown in Tables 1-3. Note that energy streams Q1 and Q2 actually represent the rates of heating and cooling of the beds of solids, where Q1 represents the heating or cooling of the heat transfer solids and Q2 represents the heat or cooling of the reforming catalyst. For example, the average rate of cooling of the heat transfer solids bed represented by E-1 is the same as the average rate of heating of the heat transfer solids bed represented by E-2.

TABLE 1

(Stream Characteristics)

| Stream Characteristic | Stream No. | | | | | | | |
|---|---|---|---|---|---|---|---|---|
| | 501 | 502 | 503 | 504 | 505 | 506 | 507 | 508 |
| Phase | Vapor | Vapor | Vapor | Vapor | Vapor | Vapor | Vapor | Vapor |
| Temp (° C.) | 100.0 | 242.5 | 280.0 | 345.1 | 1010.0 | 835.8 | 1053.7 | 518.0 |

TABLE 1-continued (Stream Characteristics)

| Stream Characteristic | Stream No. | | | | | | | |
|---|---|---|---|---|---|---|---|---|
| | 501 | 502 | 503 | 504 | 505 | 506 | 507 | 508 |
| Press. (bar) | 35 | 35 | 35 | 35 | 35 | 35 | 35 | 35 |
| Flowrate (kg-mol/hr) | 100.0 | 76.2 | 46.1 | 180.8 | 180.8 | 248.6 | 368.1 | 368.1 |
| Total Mass Rate (kg/hr) | 1738.3 | 1372.8 | 1471.5 | 3111.1 | 3111.1 | 3111.1 | 4582.6 | 4582.6 |
| Total Mol Wt. | 17.38 | 18.02 | 31.92 | 17.21 | 17.21 | 12.51 | 12.45 | 12.45 |

TABLE 2

(Stream Composition; moles)

| Component | Stream No. | | | | | | | |
|---|---|---|---|---|---|---|---|---|
| | 501 | 502 | 503 | 504 | 505 | 506 | 507 | 508 |
| $H_2O$ | 0.0000 | 1.0000 | 0.0000 | 0.3961 | 0.3961 | 0.1302 | 0.1595 | 0.1595 |
| $N_2$ | 0.0480 | 0.0000 | 0.0200 | 0.0265 | 0.0265 | 0.0193 | 0.0155 | 0.0155 |
| CO | 0.0000 | 0.0000 | 0.0000 | 0.0000 | 0.0000 | 0.1148 | 0.2259 | 0.2259 |
| $O_2$ | 0.0000 | 0.0000 | 0.9800 | 0.0000 | 0.0000 | 0.0000 | 0.0000 | 0.0000 |
| $CO_2$ | 0.0001 | 0.0000 | 0.0000 | 0.0217 | 0.0127 | 0.0308 | 0.0335 | 0.0335 |
| Methane | 0.8975 | 0.0000 | 0.0000 | 0.5439 | 0.5439 | 0.2591 | 0.0139 | 0.0139 |
| Ethane | 0.0544 | 0.0000 | 0.0000 | 0.0000 | 0.0000 | 0.0001 | 0.0000 | 0.0000 |
| $H_2$ | 0.0000 | 0.0000 | 0.0000 | 0.0207 | 0.0207 | 0.4458 | 0.5515 | 0.5515 |
| Graphite | 0.0000 | 0.0000 | 0.0000 | 0.0000 | 0.0000 | 0.0000 | 0.0000 | 0.0000 |

TABLE 3

(Stream Composition Flow Rate; kg-mol/hr)

| Component | Stream No. | | | | | | | |
|---|---|---|---|---|---|---|---|---|
| | 501 | 502 | 503 | 504 | 505 | 506 | 507 | 508 |
| $H_2O$ | 0.0000 | 76.200 | 0.000 | 71.609 | 71.609 | 32.356 | 58.724 | 58.724 |
| $N_2$ | 4.8000 | 0.000 | 0.920 | 4.800 | 4.800 | 4.800 | 5.722 | 5.722 |
| CO | 0.0000 | 0.000 | 0.000 | 0.006 | 0.006 | 28.546 | 83.168 | 83.168 |
| $O_2$ | 0.0000 | 0.000 | 45.178 | 0.000 | 0.000 | 0.000 | 0.000 | 0.000 |
| $CO_2$ | 0.0100 | 0.000 | 0.000 | 2.302 | 2.302 | 7.659 | 12.342 | 12.342 |
| Methane | 89.750 | 0.000 | 0.000 | 98.327 | 98.327 | 64.402 | 5.130 | 5.130 |
| Ethane | 5.440 | 0.000 | 0.000 | 0.002 | 0.002 | 0.017 | 0.000 | 0.000 |
| $H_2$ | 0.0000 | 0.000 | 0.000 | 3.750 | 3.750 | 110.810 | 203.035 | 203.035 |
| Graphite | 0.0000 | 0.000 | 0.000 | 0.000 | 0.000 | 0.0000 | 0.000 | 0.000 |

In particular, the data in Tables 1-3 show that the heat transfer rates provide stream temperatures that allow heat to flow in the proper direction and also provide thermodynamic equilibrium compositions that are desirable for the production of methanol.

Having now fully described this invention, it will be appreciated by those skilled in the art that the invention can be performed within a wide range of parameters within what is claimed, without departing from the spirit and scope of the invention.

What is claimed is:

1. A process for producing synthesis gas comprising:
   a) flowing a hydrocarbon- and water-containing feed gas mixture across a first bed of hot solids to heat the gas;
   b) flowing the heated gas through a first oxidation zone;
   c) flowing the heated gas exiting the first oxidation zone across at least one reforming zone to form a synthesis gas;
   d) flowing the synthesis gas through a second oxidation zone;
   e) flowing the synthesis gas from the second oxidation zone across a second bed of solids to heat the second bed of solids and cool the synthesis gas wherein in at least one of oxidation zones (b) and (d) an oxygen-containing gas is introduced into the oxidation zone to produce syngas and generate heat;
   f) reversing the direction of flow of the feed gas mixture at intermittent intervals; and
   g) recovering synthesis gas from the process in both directions of flow of the feed gases.

2. The process of claim 1 wherein the synthesis gas leaving the at least one reforming zone is maintained at a temperature of at least 750° C. when no oxygen-containing gas has been injected into the first oxidation zone.

3. The process of claim 1 wherein the synthesis gas leaving the at least one reforming zone is maintained at a temperature of at least 900° C. when oxygen-containing gas has been injected into the first oxidation zone.

4. The process of claim 1 wherein the synthesis gas leaving the second bed of solids is maintained at a temperature of not greater than about 650° C.

5. The process of claim 1 wherein, depending on the direction of flow of the hydrocarbon and water-containing feed as mixture, the feed gas mixture flowed across the first bed of solids or the second bed of solids is heated to a temperature of at least 900° C.

6. The process of claim 1 wherein the heated gas enters the at least one reforming zone at a mole ratio of steam to hydrocarbon of from 0.4:1 to 5:1.

7. The process of claim 6 wherein gas leaving the at least one reforming zone has a molar ratio of hydrogen to carbon oxide of from 1:1 to 5:1.

8. The process of claim 1 wherein oxygen-containing gas is introduced into the second oxidation zone.

9. The process of claim 1 wherein oxygen-containing gas is introduced into the first oxidation zone.

10. The process of claim 1 wherein oxygen-containing gas is introduced into the first oxidation zone and into the second oxidation zone.

11. A process for producing synthesis gas, comprising:
   a) flowing a hydrocarbon and water-containing feed gas across a first bed of hot solids to heat the feed gas;
   b) flowing the heated feed gas across at least one first reforming zone to form a reformed gas;
   c) flowing the reformed gas through an oxidation zone into which is injected an oxygen-containing gas to oxidize at least a portion of the reformed gas to form synthesis gas;
   d) flowing the partially oxidized reformed gas from the oxidation zone into a second reforming zone containing reforming catalyst to convert at least a portion of unconverted hydrocarbon in the synthesis gas into additional synthesis gas; and
   e) flowing the synthesis gas across a second bed of solids to heat the second bed of solids and cool the synthesis gas;
   f) reversing the direction of flow of the feed gas at intermittent intervals; and
   g) recovering synthesis gas from the process in both directions of flow of the feed gas.

12. The process of claim 11 wherein the synthesis gas that leaves the second bed of reforming catalyst is maintained at a temperature of at least 900° C.

13. The process of claim 11 wherein the gas flowed across the beds of solids is heated, depending on the direction of flow, to a temperature of at least 900° C.

14. The process of claim 11 wherein the reforming gas that leaves the first bed of refonning catalyst is maintained at a temperature of at least 750° C.

15. The process of claim 11 wherein the synthesis gas tat leaves the second bed of solids is maintained at a temperature of not greater than about 650° C.

16. The process of claim 1 or 11, wherein the reforming catalyst comprises at least one active metal or metal oxide of Group 6 or Group 8 to 10 of the Periodic Table of the Elements.

17. The process of claim 1 or 11, wherein the solids are refractory inorganic oxide solids.

18. The process of claim 1 or 11, wherein the first and second beds of solids are in separate vessels.

19. The process of claim 1 or 11, wherein the hydrocarbon comprises methane.

* * * * *